(12) United States Patent
Steinberg

(10) Patent No.: US 6,810,107 B2
(45) Date of Patent: Oct. 26, 2004

(54) SYSTEM AND METHOD FOR MEASURING BEAM QUALITY AND DOSIMETRY USING ELECTRONIC PORTAL IMAGING

(75) Inventor: Todd H. Steinberg, Antioch, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 103 days.

(21) Appl. No.: 10/053,369

(22) Filed: Nov. 2, 2001

(65) Prior Publication Data

US 2003/0095625 A1 May 22, 2003

(51) Int. Cl.[7] .................................................. A61N 5/10
(52) U.S. Cl. ....................................................... 378/65
(58) Field of Search ........................................... 378/65

(56) References Cited

U.S. PATENT DOCUMENTS

| 4,995,068 A | 2/1991 | Chou et al. |
| 5,138,647 A | 8/1992 | Nguyen et al. ............. 378/189 |
| 5,233,990 A | 8/1993 | Barnea ..................... 128/653.1 |
| 5,712,482 A | 1/1998 | Gaiser et al. .......... 250/363.08 |
| 5,754,622 A | 5/1998 | Hughes ....................... 378/65 |
| 5,784,431 A * | 7/1998 | Kalend et al. ................ 378/65 |
| 6,282,264 B1 | 8/2001 | Smith et al. |
| 6,345,114 B1 * | 2/2002 | Mackie et al. ................ 378/65 |

OTHER PUBLICATIONS

Clinical Use of Electronic Portal Imaging: Report of AAPM Radiation Therapy Committee Task Group 58, Michael G. Herman, et al., Medical Physics, May 2001, AIP For American Assoc. Phys. Med, USA, vol. 28, No. 5, pp. 712–737, XP002262818, ISSN: 0094–2405, p. 732: Section V, D Advanced Applications.

* cited by examiner

Primary Examiner—Harshad Patel

(57) ABSTRACT

A radiation therapy device including a linear accelerator (20) for providing radiation to a body; and an electronic portal imaging device (90) operably coupled to the linear accelerator. The electronic portal imaging device (90) is adapted for use in commissioning the radiation therapy device and adapted for use in dosimetry applications during therapy.

17 Claims, 11 Drawing Sheets

SYSTEM AND METHOD FOR MEASURING BEAM QUALITY AND DOSIMETRY USING ELECTRONIC PORTAL IMAGING

CROSS REFERENCE TO RELATED APPLICATION

The present application is related to co-pending U.S. patent application Ser. No. 10/053,283 titled "SYSTEM AND METHOD FOR POSITIONING AN ELECTRONIC PORTAL IMAGING DEVICE," filed concurrently.

BACKGROUND OF THE INVENTION

The present invention relates to a radiation emitting device, and more particularly, to a system and method for evaluating beam quality during therapy using electronic portal imaging.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

One step in treatment planning is the characterization of all beams produced by the linear accelerator or commissioning of the treatment machine. This typically involves establishment of beam data tables for the machine using an ionization chamber and a water phantom. The beam data includes relative beam profiles and absolute dosimetric quantities under varying machine conditions (e.g., field sizes, energies, beam modifiers, dose rates, setup conditions, etc.). Once the data have been collected, they are used to set up the beam data tables and input to commission the treatment planning computer used for dose calculations.

SUMMARY OF THE INVENTION

A radiation therapy device according to an embodiment of the present invention includes a linear accelerator for providing radiation to a body; and an electronic portal imaging device operably coupled to the linear accelerator. The electronic portal imaging device is adapted for use in commissioning the radiation therapy device and adapted for use in dosimetry applications during therapy

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 1:
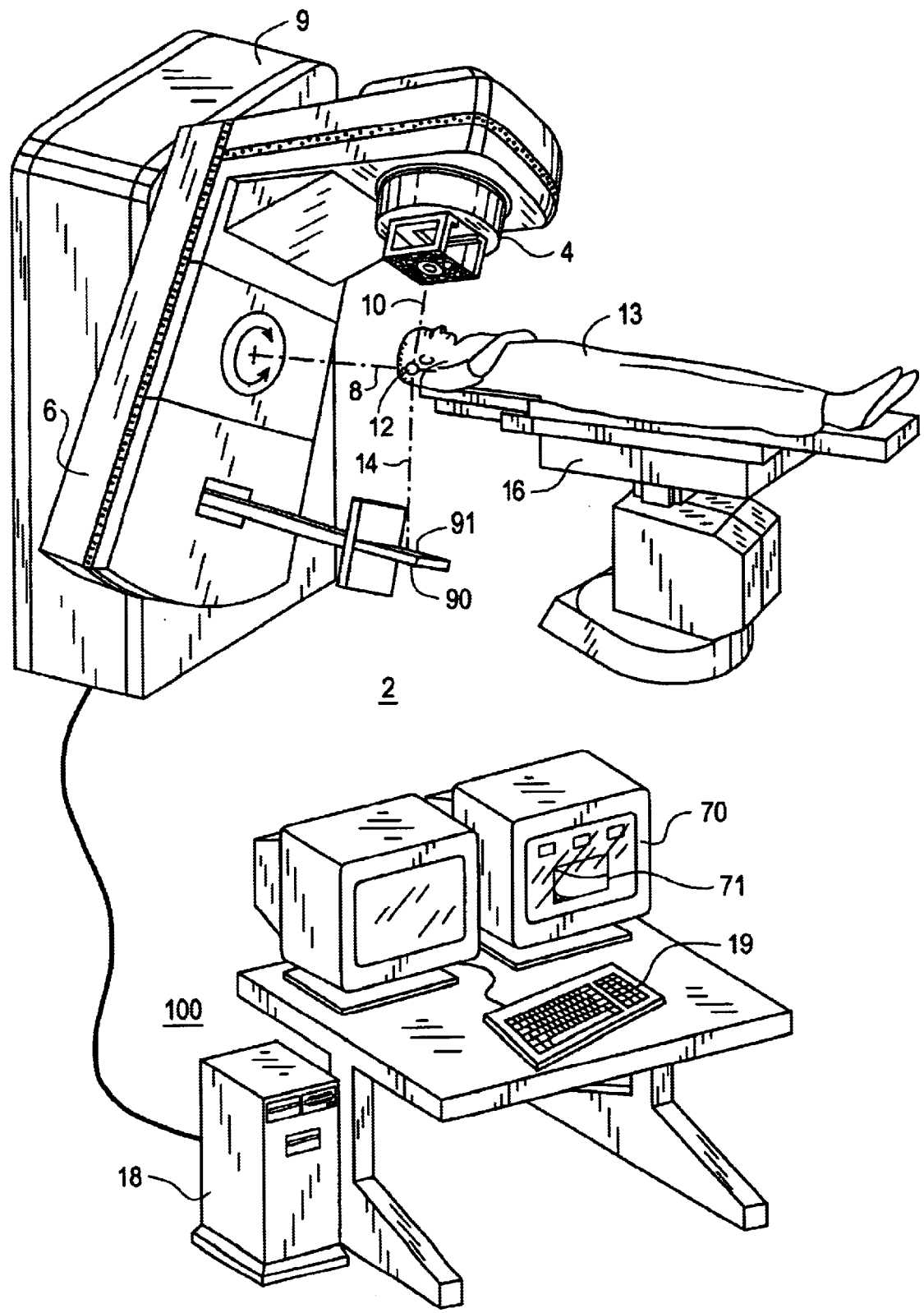
FIG. 1 is a diagram of a radiation treatment device according to an embodiment of the present invention.

Turning now to the drawings and, with particular attention to FIG. 1, a radiation treatment apparatus embodying the present invention is shown therein and generally identified by reference numeral 2. The radiation treatment apparatus 2 includes a beam shielding device (not shown) within a treatment head 4, a control unit in a housing 9 and a treatment unit 100. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter. Exemplary radiation treatment devices suitable for use with the teachings of the present invention are the Mevatron and Primus systems, available from Siemens Medical Systems, Inc.

A beam shielding device, such as one or more plates, may be provided within the treatment head. Such plates are substantially impervious to the emitted radiation. The plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

It is noted that plates, although common, are not the only type of beam shielding devices available. For example, many radiation therapy devices include some form of beam collimator, wedge, compensator, jaw and/or other aperture device. An aperture device itself can act as the beam shielding device and the various beam shielding devices can be combined to limit the delivered radiation. The present invention can be used with any such arrangement and can also be used in dynamic conformal treatments in which the gantry, collimator, jaws and multileaf collimators could all be in motion during the radiation delivery.

The radiation treatment device 2 also includes a central treatment processing or control unit 100 which is typically located apart from the radiation treatment device 2. The radiation treatment device 2 is normally located in a different room to protect the therapist from radiation. The treatment unit 100 includes output devices such as at least one visual display unit or monitor 70 and an input device such as a keyboard 19. Data can be input also through data carriers such as data storage devices or a verification and recording or automatic setup system.

The treatment processing unit 100 is typically operated by the therapist who administers actual delivery of radiation treatment as prescribed by an oncologist by using the keyboard 19 or other input device. The therapist enters into the control unit of the treatment unit 100 the data that defines the radiation dose to be delivered to the patient, for example, according to the prescription of the oncologist. The program can also be input via another input device, such a data storage device. Various data can be displayed before and during the treatment on the screen of the monitor 70.

In addition, a portal imaging system 90 may be attached to the gantry 6. Because the portal imaging system 90 is mounted on the gantry 6, portal images can be obtained at any gantry angle and during rotation of the gantry 6. The portal imaging system may include a flat panel, amorphous silicon detector implemented as one or more arrays of photosensitive sensors.

The portal imaging system includes a detector unit 91 capable of measuring the radiation exiting the object 13. The amount of radiation exiting object 13 can be used to verify the radiation treatment in a treatment mode. Thus, the detector unit 91 is used to gather the patient's exit dose information. The radiation dose is then reverse calculated by the CPU 18. The delivered radiation dose is then compared to the planned delivery dose. If these dose amounts match, the prescription was executed as planned. If the amounts do not match, measures can be taken for correction.

In one embodiment of the present invention, the exit dose is displayed on the screen of monitor 70 in a display area 71 which can cover the entire screen. Various other data can also be displayed before, during and after treatment on monitor 70. Thus, display area 71 can cover a portion of the screen and can be designed as a window or as an icon. In addition to the measured delivered radiation, the prescribed radiation can also be shown on the screen. The display of the measured delivered radiation may be carried out in real time. Thus, at any time during treatment, the amount of delivered radiation can be verified. In addition, at the end of a treatment, the overall delivered radiation can be verified with the prescribed radiation. This can be initiated automatically with a software program capable of detecting the end of a treatment, or this can be initiated manually by, for example, a therapist. Instead of or in addition to monitor 70, other output devices, such as a printer, can be utilized.

In addition, the portal imaging system 90 allows characterization of all beams produced by the system 2 in a characterization or physics mode. The beam data includes relative beam profiles and absolute dosimetric quantities with varying machine conditions (fields sizes, energies, beam modifiers, dose rates, setup conditions, etc.). Once the data has been collected, it is used to set up dosimetry tables and input used to commission the treatment planning computer used for dose calculations.

Figure 2:
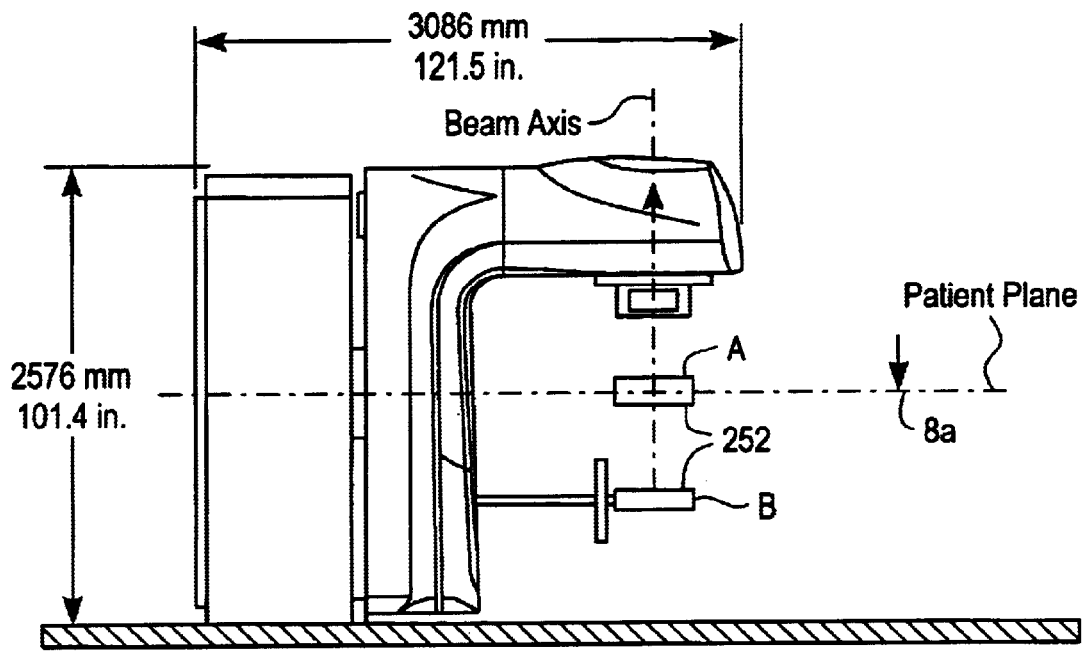
FIG. 2 is a diagram illustrating the adjustability of a portal imaging device positioner according to an embodiment of the present invention.

To properly commission the medical linac, data must be collected under normal clinical conditions of the machine. This data must be collected at various depths with respect to the isocentric plane. A portal imaging system 90 according to embodiments of the present invention allows both commissioning the linac and measurement of patient exit dosimetry. More particularly, as will be explained in greater detail below, the portal imaging device platform 252 is adjustable in a vertical direction and, as such, is usable for both device commissioning and patient dosimetry. That is, as shown in FIG. 2, the portal imaging device platform 252 and the associated imaging panel is adjustable in a position A in the patient plane 8a, for use in commissioning the machine, and in a position B for use in dosimetry. While any suitable mechanism may be employed to adjust the imaging panel into position, one such mechanism is described in concurrently filed, co-pending U.S. patent application Ser. No. 10/053,283, titled "SYSTEM AND METHOD FOR POSITIONING AN ELECTRONIC PORTAL IMAGING DEVICE," which is hereby incorporated by reference in its entirety as if fully set forth herein.

Figure 3:
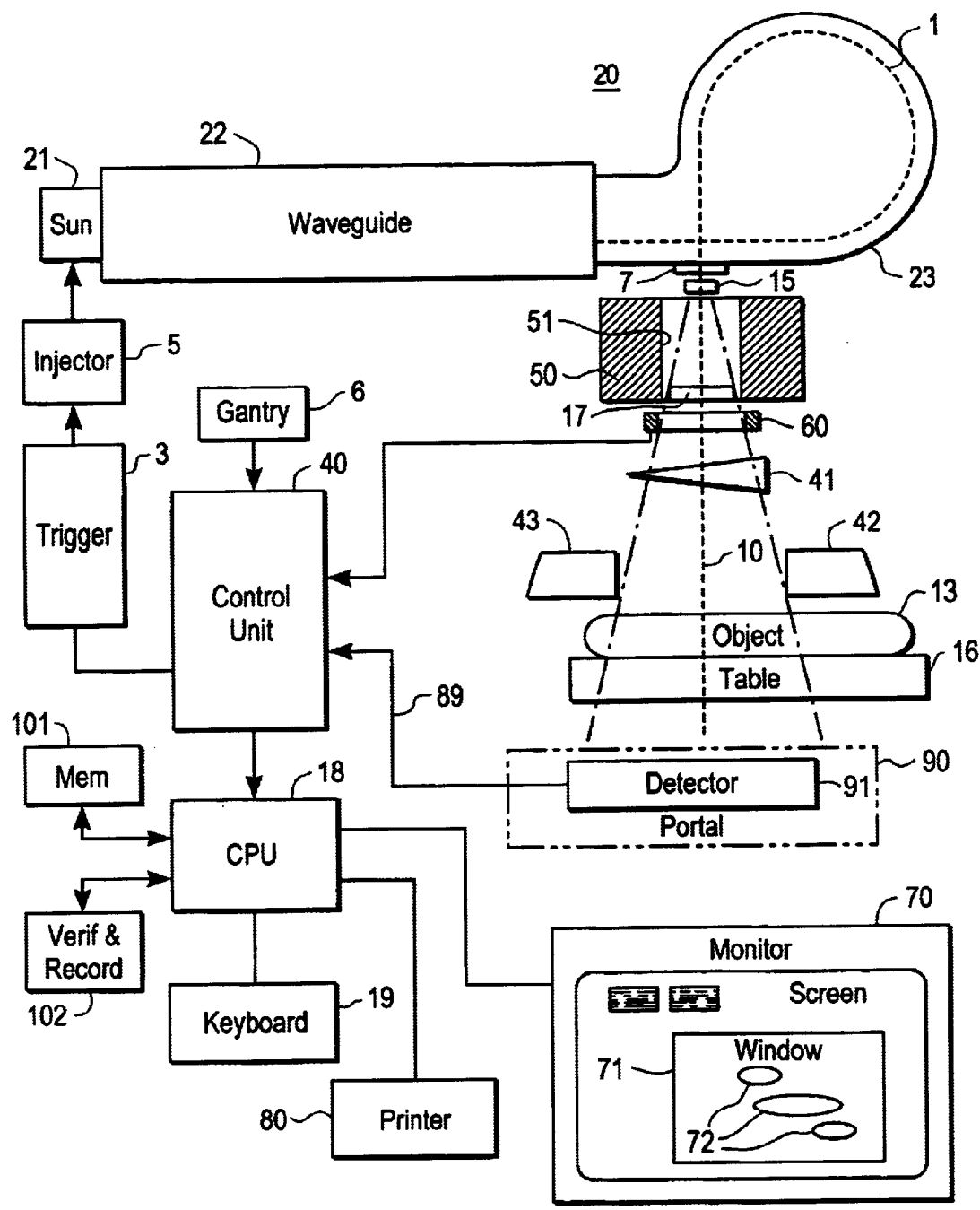
FIG. 3 is a block diagram illustrating portions of a processing unit, a control unit, and a beam generation unit for the radiation treatment device of FIG. 1.

FIG. 3 shows portions of radiation treatment device 2 and portions of treatment unit 100 in more detail. An electron beam 1 (also referred to as a radiation beam) is generated in an electron accelerator 20. Accelerator 20 includes an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in the accelerator 20 for generating the electron beam 1. The electron beam 1 is accelerated and guided by wave guide 22. For this purpose, a high frequency (HF) source is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the radiation dose is ascertained. If the radiation beam is an x-ray beam, the scattering foils are replaced by a target. A wedge filter 41 and aperture plates 42 and 43 can be provided in the path of radiation beam 1 such that the radiation is focused on the area to be irradiated. As noted above, this is just one example of a beam-shielding arrangement that can be used in the present invention.

As stated above, a detector unit 91 is arranged beneath object 13 from the viewpoint of the beam source. In one embodiment, detector unit 91 is located within portal imaging system 90. The amount of the radiation beam delivered to object 13 is measured by detector unit 91 such that radiation is sensed after it has passed through object 13.

FIG. 3 also shows various portions of the treatment unit 100. Monitor 70 and keyboard 19 are connected to CPU 18.

A printer 80 can also be provided to record information related to the treatment. CPU 18 is programmed to assist in the control of radiation treatment device 2. According to the instructions of the oncologist, the therapist programs CPU 18, so that it carries out the prescribed course(s) of radiation treatment. In window 71 on the screen of monitor 70, curves 72 indicate the prescribed delivery of the radiation treatment. A memory 101 along with a verification and recording system 102 can be connected to CPU 18.

A control unit 40 receives position information from gantry 6, and it receives information about radiation emission from measuring chamber 60. Detector unit 91 provides exit radiation signals 89 to control unit 40. These exit radiation signals 89 include information about the amount of radiation which has passed through object 13. CPU 18 processes signals received from control unit 40 and reverse calculates the incident beam for the distributed radiation. In one embodiment, this incident beam is based on exit radiation signals 89 and on attenuation factors (e.g., the anatomical attenuation factors of object 13). The incident beam can also be based on exit radiation signals 92 alone. CPU 18 can then output a two dimensional or a three dimensional display of a radiation delivered dose map. This radiation map can be in the form of radiation dose curves 72 which provide a three dimensional display. The radiation map displays the measured amount of radiation which has been distributed through-object 13. Additionally, other curves, such as curves representing the planning system dose and/or icons related to a wedge function, can also be displayed on monitor 70.

In addition to the patient exit dosimetry described above, a system according to embodiments of the present invention may be used for relatively easy commissioning of an associated medical linac. As noted above, properly commissioning the linac requires acquisition of a large amount of data under normal clinical conditions of the machine and, in particular, with respect to the isocentric plane 8a (FIG. 2).

More particularly, as will be explained in greater detail below, a portal imaging device 90 according to embodiments of the present invention, may be used to obtain beam profiles such as dose depth curves and field size.

Figure 4:
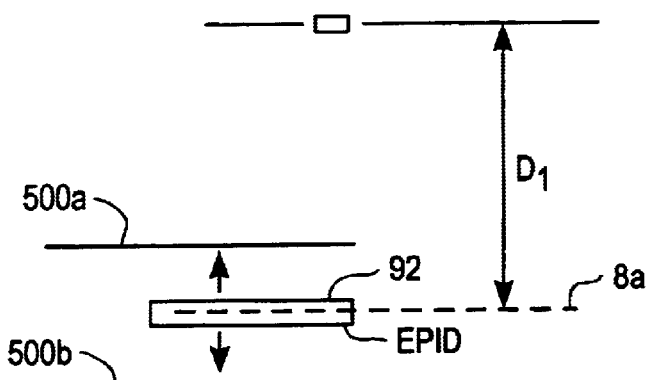
FIG. 4 is a diagram schematically illustrating device positioning during linac commissioning according to an embodiment of the present invention.

A portal imaging device according to embodiments of the present invention is used to commission the machine at the various depths by being adjustable through the patient plane 8a. More particularly, FIG. 4 illustrates schematically operation of the portal imaging device during beam commissioning.

Shown are the guide window 7 and imaging panel 92. The imaging panel 92 is positioned at the patient plane 8a, a distance or depth D1 from the window 7. In dosimetry applications, i.e., during patient treatment, the imaging panel is fixed at plane 502, a predetermined distance below the patient plane 8a.

During beam commissioning, the imaging panel 92 may be positioned at the patient plane 8a, but also may be positioned within the range 500a–500b. The detector unit 91 (FIG. 3) then provides signals indicative of the delivered dose at the given position to the control unit 40, which also receives signals from the measurement unit 60, and gantry and beam blocking device information. The control unit 40 provides these signals to the CPU 18 which then collates the information into various tables and graphs for use in the dosimetry calculations during treatment.

Figure 5A:
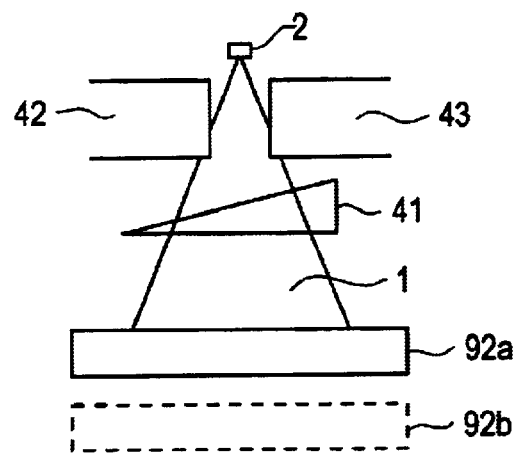
FIG. 5A–FIG. 5C illustrate exemplary device settings used during beam commissioning.
Figure 5B:
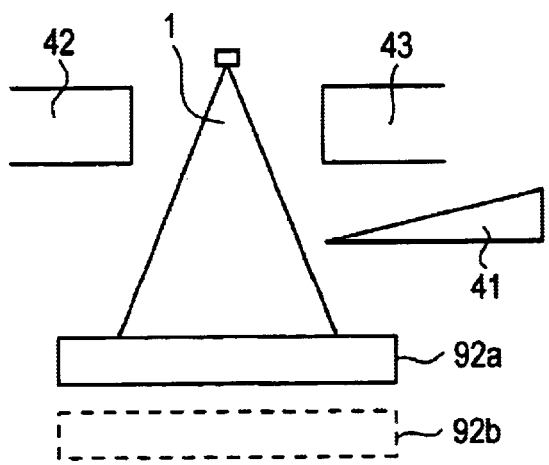
Figure 5C:
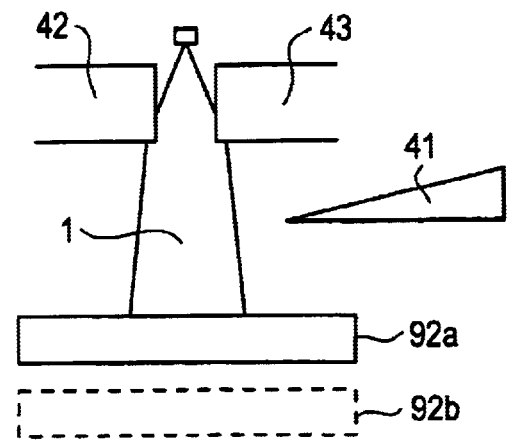

For example, FIG. 5A–FIG. 5C illustrate exemplary system configurations for system commissioning. For example, FIG. 5A illustrates a radiation beam 1 being emitted from window 7. Beam shielding plates 42, 43 are placed in a predetermined position in a path of the beam 1 to delimit the beam. Similarly, a wedge filter 41 is placed in the position of the beam to affect the dose distribution. In addition, the imaging panel is placed in position 92a to allow the detector 91 (FIG. 3) to measure the applied dose and store the corresponding data. The imaging panel 92 may also be moved vertically, for example, to a position 92b, for similar measurements to be taken. In practice, for each setting of the plates 42, 43 and the wedge 41, the imaging panel 92 may be moved to a variety of positions.

Once the measurements at a particular plate and wedge setting have been obtained, the wedge 41 and plates 42, 43 may be repositioned for further measurements. For example, in FIG. 5B, the wedge 41 and the plates 42, 43 have been moved out of the way of the beam 1. Again, measurements at positions 92a, 92b for example, may be obtained and stored. Similarly, in FIG. 5C, the plates 42, 43 are moved to delimit the beam 1, but the wedge 41 remains out of the way. Again, the imaging panel and detector acquire images and obtain measurements in a variety of positions, such as positions 92a, 92b.

It is noted that additional beam shielding devices, such as the leaves of a multi-leaf collimator may also be used to delimit the emitted beam 1 during commissioning. Further, complete system commissioning typically also requires obtaining measurements at a variety of gantry settings and beam energies. This, the figures are exemplary only.

Once the measurements have been obtained by the detector 91, the control unit 40 and the detector unit 91 provide information about the amount of radiation and the system settings to the CPU 18. The CPU 18 then stores the information and uses it in treatment planning and, for example, to dose curves, and the like.

Figure 6A:
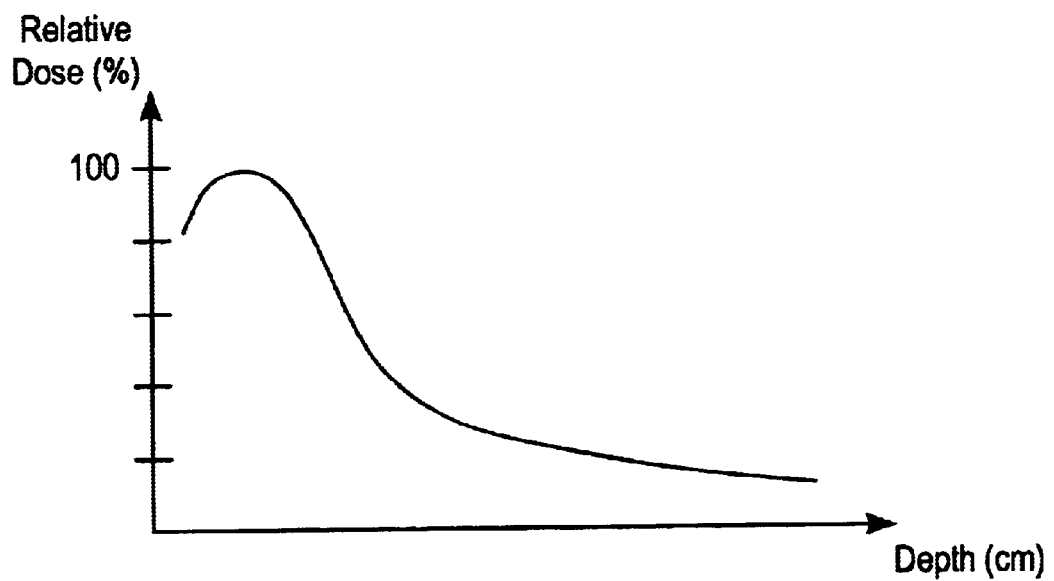
FIG. 6A and FIG. 6B illustrate graphs acquired during beam commissioning according to an embodiment of the present invention.
Figure 6B:
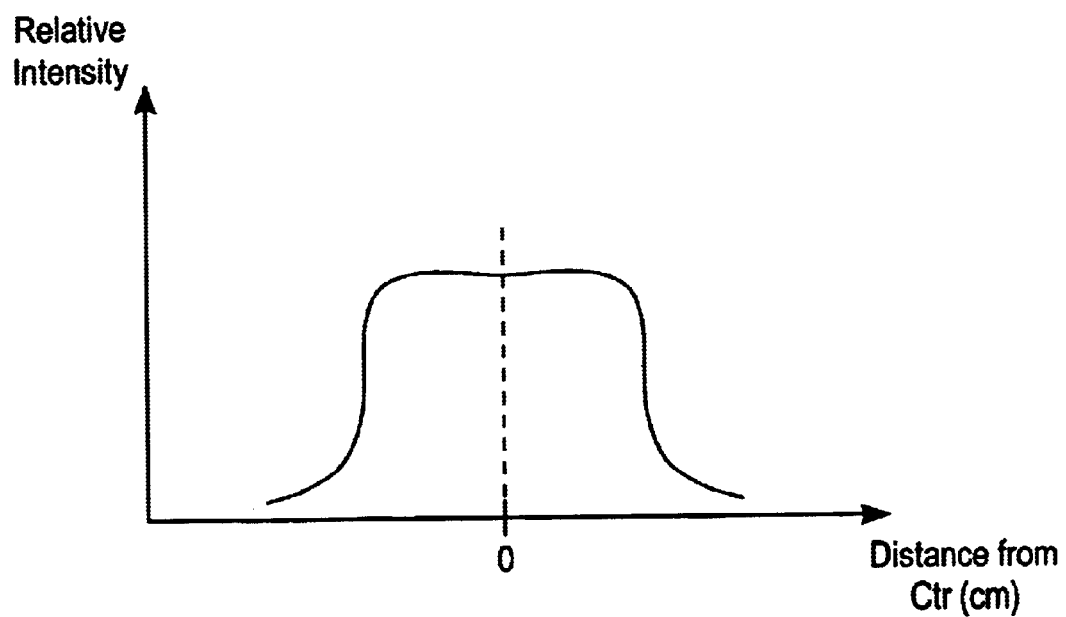

For example, FIG. 6A is a depth dose curve for a beam of a particular energy. The vertical axis is percentage depth dose and the horizontal axis is depth, where depth is relative to the patient plane 8a. In practice, a plurality of such curves will be acquired, for a plurality of beam energies. FIG. 6B is a graph of the intensity profile of the radiation beam, which is another characteristic of the linac obtained during commissioning. In particular, the graph shows the field intensity with reference to the central axis. In practice, one such graph will be obtained for many depths and field sizes for each energy.

As noted above, in operation, the electronic portal imaging device's imaging panel 92 is moved into position such that the patient 13 is between the panel and the radiation source. The detector 91 then collects an exit dose and, using the exit dose and attenuation information and other data obtained during system commissioning, the CPU 18 performs a reverse calculation to determine the incident beam from the radiation source. A delivered radiation map is generated and the dose requirements and the measured exit dose are used to verify the amount of radiation delivered to the patient 13. An exemplary system for verifying the amount of radiation delivered to a body is described in commonly assigned U.S. Pat. No. 5,754,622, which is hereby incorporated by reference in its entirety as if fully set forth herein.

A portal imaging device according to embodiments of the present invention allows for absolute as well as relative dosimetry measurements. Relative dosimetry includes those beam profile and depth dose profile measurements that are either normalized to the central axis or to the depth of maximum dose. Absolute dosimetric measurements are those patient exit dose measurements that can be converted to absolute dose (cGy). A portal imaging device according to embodiments of the present invention allows the positioning of the flat panel such that either absolute or relative dosimetry measurements may be made. The absolute measurement may be made real time during a patient treatment and can be used as a feedback to the control system of the machine for proper treatment delivery.

Figure 7:
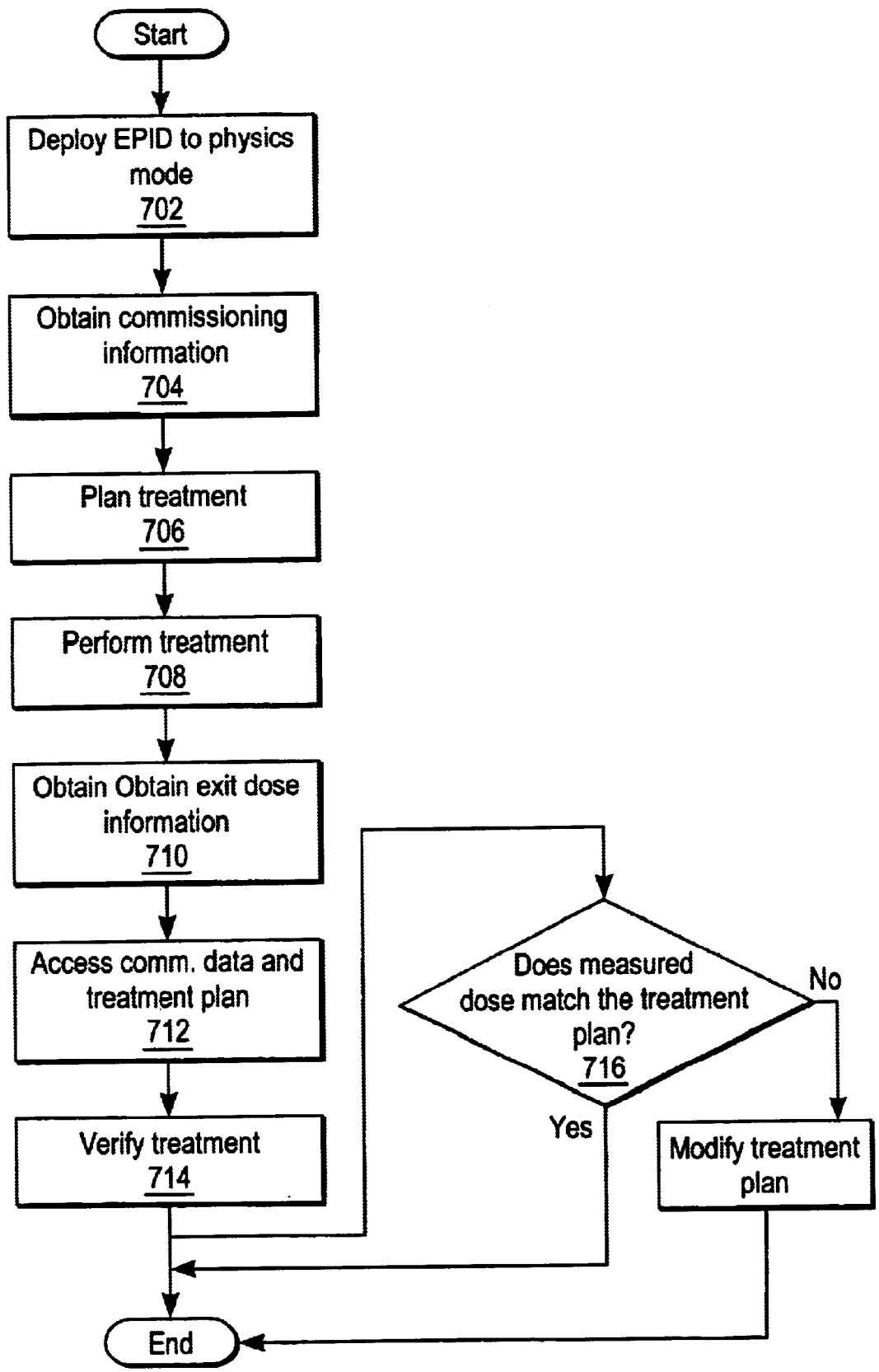
FIG. 7 is a flowchart illustrating operation of an embodiment of the present invention.

Turning now to FIG. 7, a flowchart illustrating operation of an embodiment of the present invention is shown. In a step 702, the electronic portal imaging device is deployed to a physics mode. Thus, the imaging panel 92 is moved from the treatment position to a position at or near the patient plane 8a. In step 704, the commissioning information is obtained, as radiation is applied at various energies and machine settings. The detector 91 detects the radiation and the corresponding data are stored in memory. Next, in a treatment mode, the electronic portal imaging device is deployed to a position below the patient plane, and the treatment is planned. Data corresponding to the treatment radiation fields are stored in memory. In step 708, the treatment is performed according to the stored treatment maps and fields. In step 710, the electronic portal imaging device is used to obtain exit dose information, as described above. In step 712, the stored commissioning data and treatment plan data are accessed and compared to the exit dose data. In step 714, the treatment is verified. In step 716 if the verified treatment does not match the treatment plan then the treatment is modified, in step 718. If the treatment plan and the verified treatment do match then the process is complete.

It is noted that a variety of mechanisms could be employed to position the imaging panel at the patient plane and in the dosimetry position. These include, for example, direct lift systems that do not employ the mounting cavity system described above. Thus, for example, in certain embodiments, the lifting of the imaging platform 252 itself is sufficient to position the panel from the patient dosimetry position to the patient plane. Furthermore, in other embodiments, the imaging platform 252 may be stored horizontally.

Figure 8A:
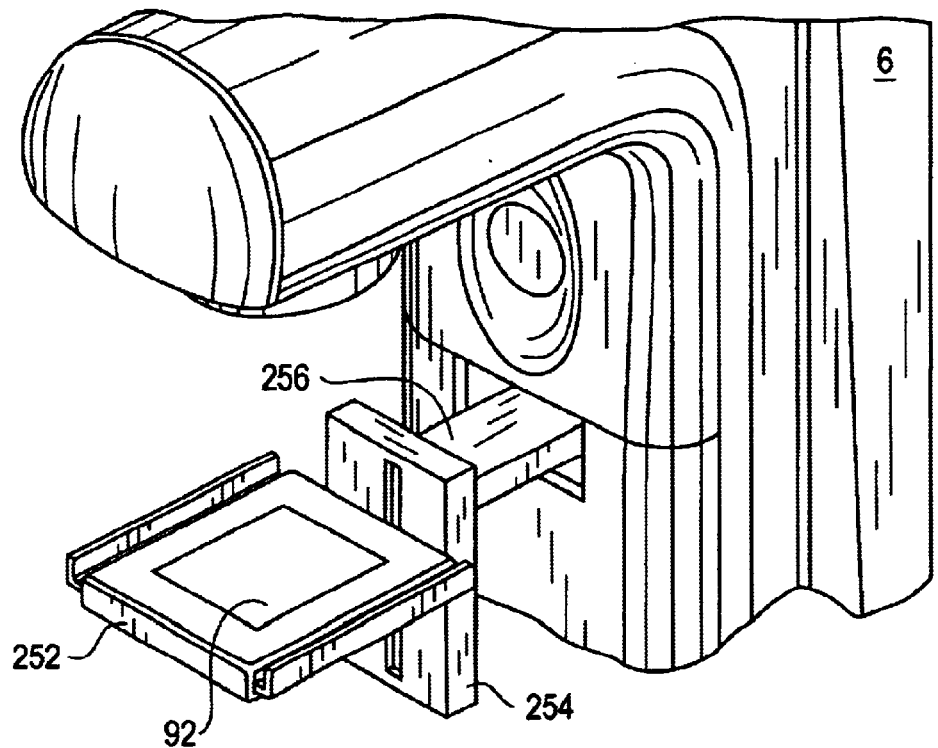
FIG. 8A and FIG. 8B illustrate a portal imaging device positioner according to an embodiment of the present invention.

Turning now to FIG. 8A, a diagram of a portal imaging device positioner according to an embodiment of the present invention is shown. The portal imaging device positioner includes a platform 252 which may be embodied as a collision bumper to protect against injury or damage. Underneath the collision bumper 252 is the EPID panel 92. The collision bumper 252 and EPID panel 92 ride vertically on the vertical drive unit or backplane 254. The backplane 254 itself can be moved in and out from the gantry. These movements are all motorized and can be controlled manually or automatically by the treatment control system 100.

Figure 8B:
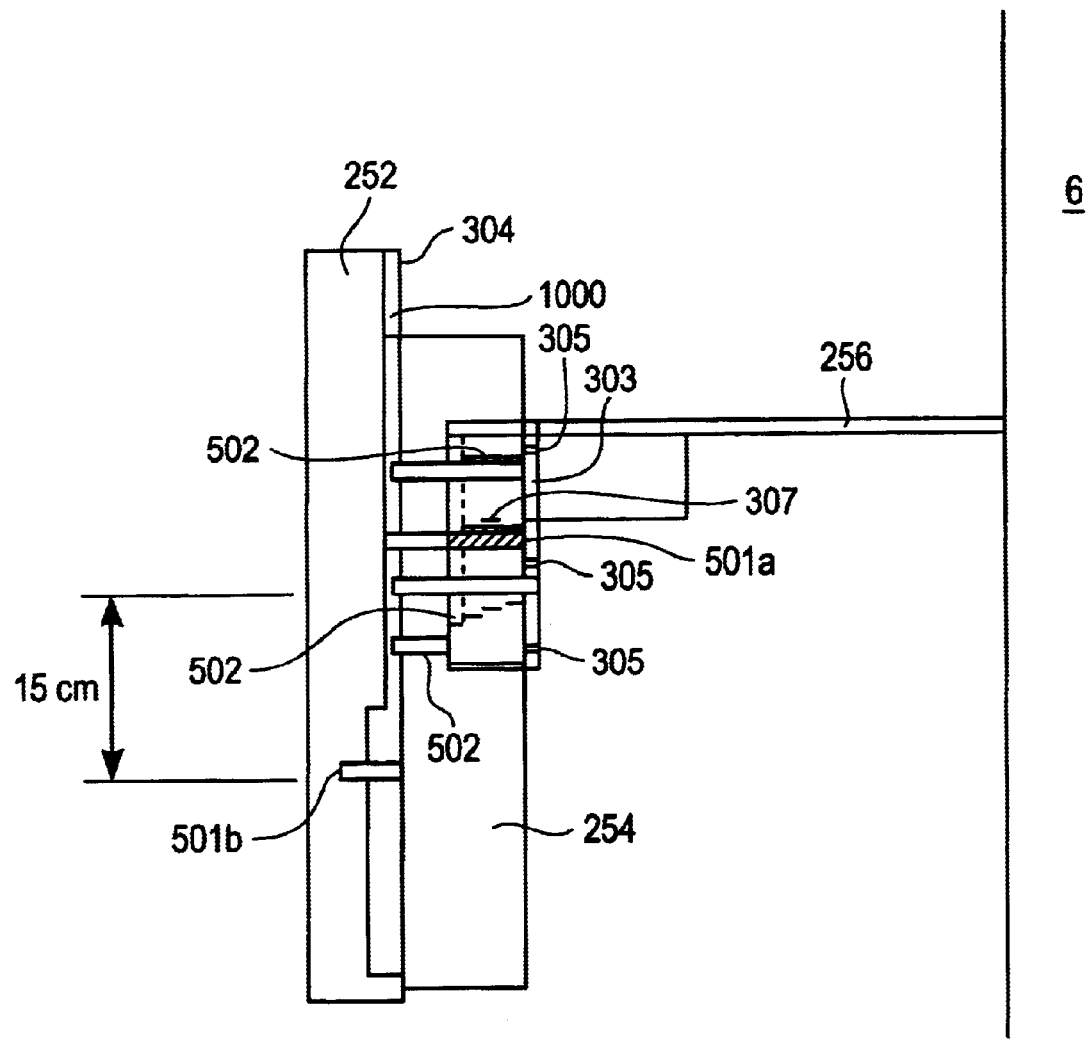

FIG. 8B illustrates various components of the portal imaging device positioner in a schematic view. As shown, the portal imaging device positioner attaches to the gantry 6 by a support such as a telescoping boom 256. A computer-controlled motor within the gantry 6 (not shown) may be used to extend and retract the portal imaging device positioner. The platform 252 mounts to the vertical drive unit 254 via the mounting unit 1000. The platform 252 is extendable into a horizontal position using one or more hinges 304. The extension into horizontal position may be accomplished using a computer-controlled motor (not shown).

In the embodiment illustrated, the vertical drive assembly 254 includes a mounting cavity 307 to allow for vertical movement of the platform 252 with respect to the telescoping boom 256. In a treatment mode, the top of the telescoping boom 256 is generally aligned with the top of the mounting cavity 307. In a physics mode, the bottom of the telescoping boom 256 is generally aligned with the bottom of the mounting cavity 307. A plurality of bolt holes 502 may be provided in the vertical drive assembly 254 to allow bolts to affix the vertical drive assembly 254 to the telescoping boom 256. Holes 501a, 501b may also be provided, to allow insertion of a "physics pin" to secure the platform 252 to the telescoping boom 256, as will be explained in greater detail below. Finally, a protective panel 303 may cover the mounting cavity 307 and may include a plurality of screw holes 305 for securing it in place.

Initially, in operation, the portal imaging device positioner is configured in a treatment mode. In this mode, the positioner is in place below the patient plane and the platform 252 can be deployed to receive radiation through the patient. The top of the telescoping boom 256 is positioned substantially adjacent the top of the mounting cavity 307.

To change to the physics mode, the platform 252 is raised with respect to the vertical drive assembly 254 and telescoping boom 256. In one embodiment, the platform 252 is raised about 15 centimeters, so that the physics pin hole portions 501a, 501b are aligned.

The protective cover 303 is then removed, to allow installation of a physics pin into the physics hole. Bolts are then removed from the bolt holes 502 to allow movement of the vertical drive assembly 254 with respect to the telescoping boom 256. The main vertical drive assembly 254 is then raised relative to the telescoping boom 256. In particular, in one embodiment, the main vertical drive assembly is raised 15 centimeters, such that the bottom of the telescoping boom 256 is substantially adjacent the bottom of the mounting cavity 307. The physics pin is then removed, the bolts replaced, and the panel can be deployed.

Adjustment of the portal imaging device positioner from treatment mode to physics mode is illustrated in greater detail with reference to FIGS. 9–14.

Figure 9:
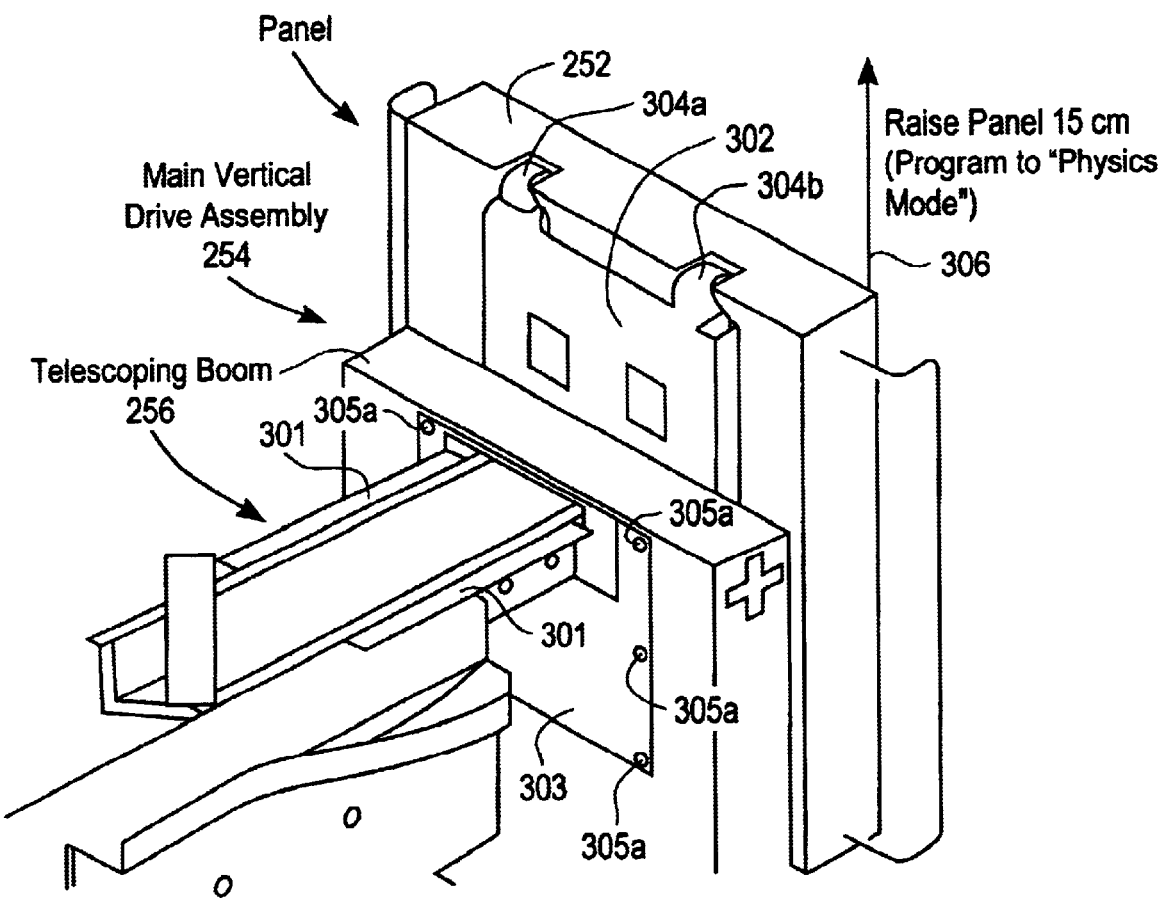
FIG. 9 is a diagram illustrating adjustment of a portal imaging device positioner according to an embodiment of the present invention.

As shown in FIG. 9, the main vertical drive assembly 254 is fixed to the telescoping boom 256 via one or more brackets 301 and a plate 303. The platform 252 attaches vertically to the main vertical drive assembly 254 via one or more hinges 304a, 304b. In operation, the platform 252 swings out horizontally on the hinges 304a, 304b, to receive radiation during both modes of operation. The platform 252 is typically stored vertically to save space. In addition, the plate 303 attaches to the main vertical drive assembly 254 via a plurality of fasteners, such as screws 305a, which fit into screw holes 305 (FIG. 8B). In on embodiment six (6) screws are provided (two of which are obscured in the figure by the telescoping boom 256).

To change the mode of operation from the treatment mode to the physics mode, the vertical drive assembly 254 is adjusted such that the platform 252 can be fixed in a higher position, i.e., in the patient plane. Initially, the platform 252 is raised from a default position to the physics position in the direction of the arrow 306. In one embodiment of the present invention, the platform 252 is raised about 15 centimeters.

Figure 10:
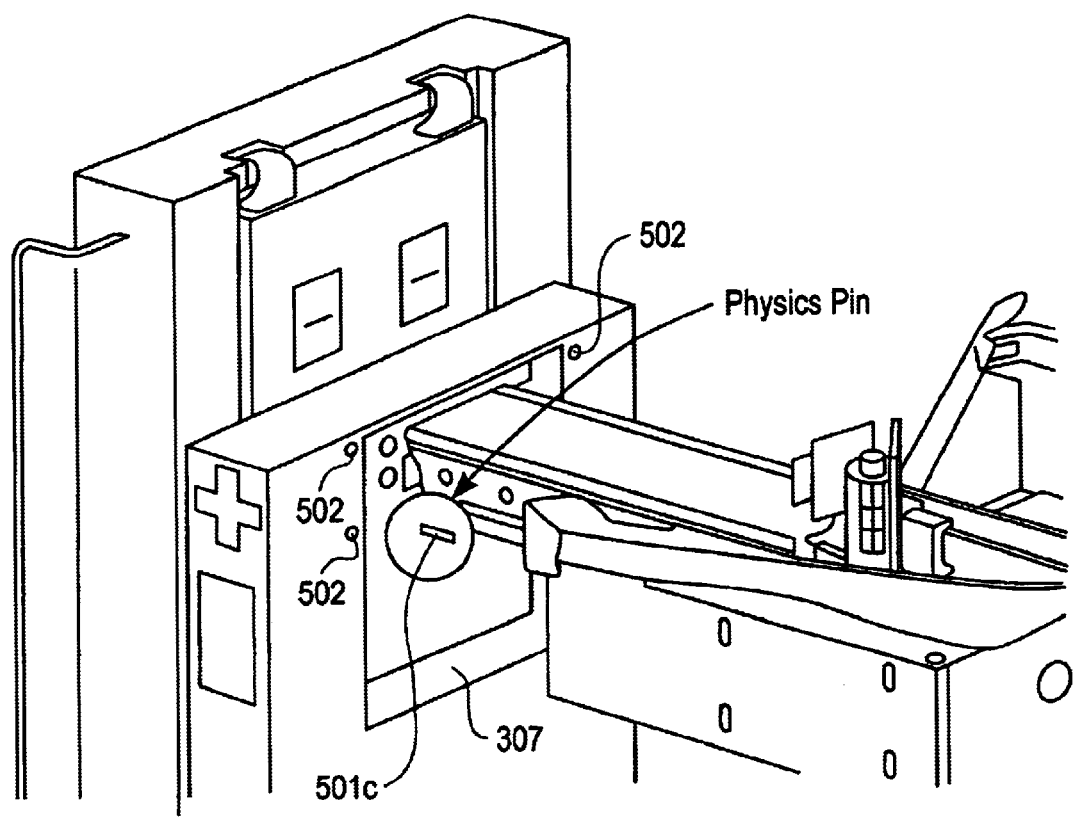
FIG. 10 is a diagram illustrating adjustment of a portal imaging device positioner according to an embodiment of the present invention.

The physics cover 303 is then removed by removing the screws 305a. As will be explained in greater detail below, this allows access to the mounting cavity 307. More particularly, as shown in FIG. 10, a "physics pin" 501c may be installed, to secure the platform 252 to the telescoping boom 256. In addition, bolts 502a that secure the vertical positioner to the telescoping arm are removed. In on embodiment of the invention, four such bolts are provided, only three of which are visible in the figure.

Figure 11:
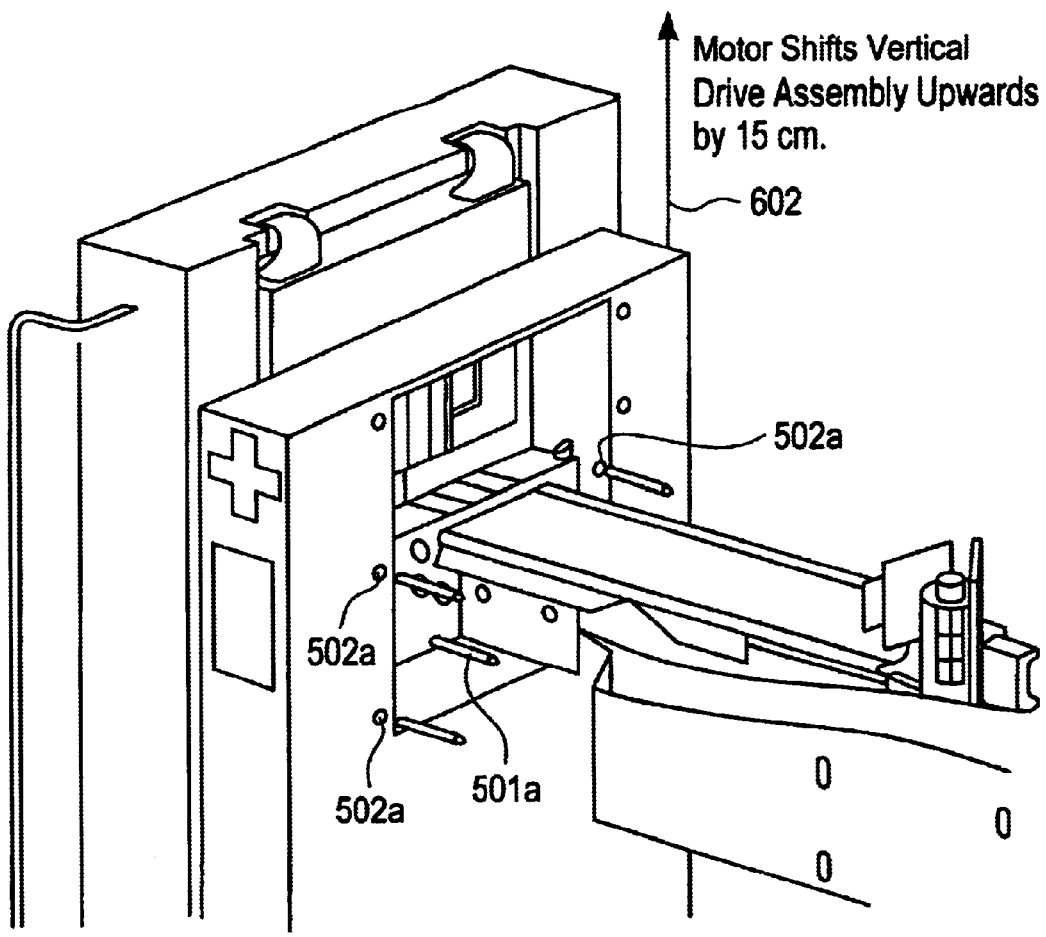
FIG. 11 is a diagram illustrating adjustment of a portal imaging device positioner according to an embodiment of the present invention.
Figure 12:
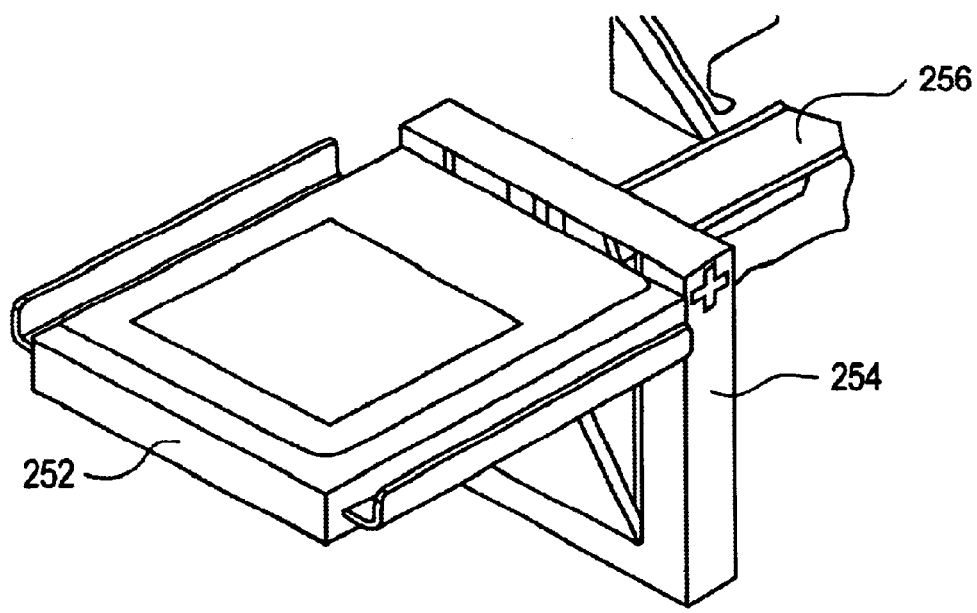
FIG. 12 is a diagram illustrating adjustment of a portal imaging device positioner according to an embodiment of the present invention.

As shown in FIG. 11, removal of the bolts 502a allows the vertical drive assembly to move in the direction of the arrow 602. The presence of the physics pin 501a means that the platform 252 is affixed to the telescoping arm. Thus, the vertical drive assembly 254 moves relative to both. Next, the bolts 502a are replaced and the physics pin 501a is removed. This fixes the vertical drive assembly 254 to the telescoping boom 256 in the physics position. Next, as shown in FIG. 12, the platform 252 may be deployed in a standby position by extending the panel along the hinges 301a, 301b.

Figure 13:
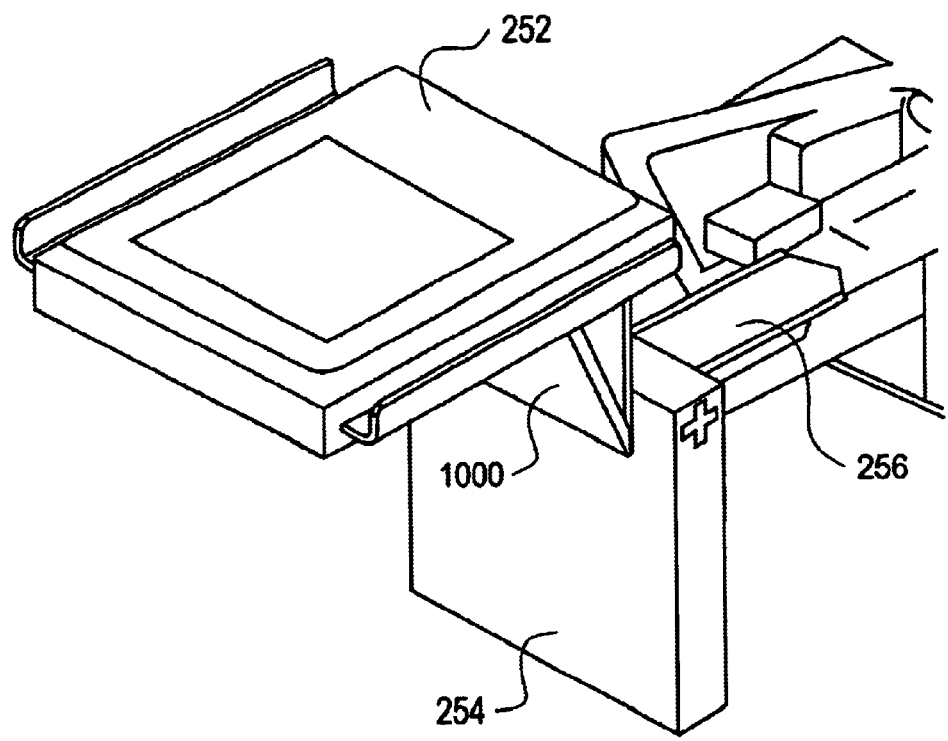
FIG. 13 is a diagram illustrating adjustment of a portal imaging device positioner according to an embodiment of the present invention.
Figure 14:
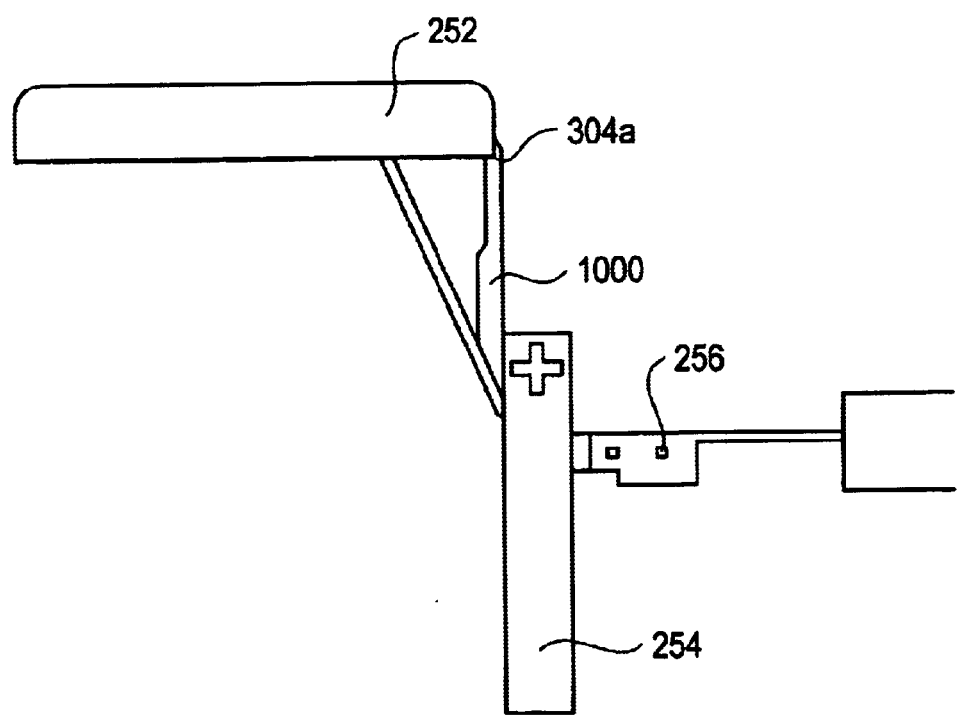
FIG. 14 is a diagram illustrating adjustment of a portal imaging device positioner according to an embodiment of the present invention.

Finally, the panel is deployed in the physics position, as shown in FIGS. 13 and 14. As shown, the portal imaging system includes the deployed horizontal platform 252, extended on the hinges 304a, b.

The invention described in the above detailed description is not intended to be limited to the specific form set forth herein, but is intended to cover such alternatives, modifications and equivalents as can reasonably be included within the spirit and scope of the appended claims.

What is claimed is:

1. A method, comprising:
   commissioning a radiation therapy apparatus using an electronic portal imaging device; and
   using said electronic portal imaging device to obtain dosimetric measurements during radiation therapy;
   wherein said electronic portal imaging device is adjustable through a patient plane.

2. A method, comprising:
   commissioning a radiation therapy apparatus using an electronic portal imaging device; and
   using said electronic portal imaging device to obtain dosimetric measurements during radiation therapy;
   wherein said commissioning comprised positioning a imaging panel of said electronic portal imaging device in a patient plane and obtaining radiation measurements at said patient plane.

3. A method according to claim 2, wherein said commissioning further comprises positioning said imaging panel at predetermined positions above and below said patient plane, and obtaining radiation measurements at said positions.

4. A method according to claim 3, wherein said using said electronic portal imaging device to obtain dosimetric measurements comprises positioning said imaging panel a predetermined distance below said patient plane and a source of radiation.

5. A radiation therapy device, comprising:
   a linear accelerator for providing radiation to a body; and
   an electronic portal imaging device operably coupled to said linear accelerator, said electronic portal imaging device adapted for use in commissioning said radiation therapy device and adapted for use in dosimetry applications during therapy;
   wherein said electronic portal imaging device is adjustable through a patient plane.

6. A radiation therapy device, comprising:
   a linear accelerator for providing radiation to a body; and
   an electronic portal imaging device operably coupled to said accelerator, said electronic portal imaging device adapted for use in commissioning said radiation therapy device and adapted for use in dosimetry applications during therapy,
   said electronic portal imaging device adapted to be deployed in a patient plane during said commissioning.

7. A radiation therapy device as recited in claim 6, said electronic portal imaging device adapted to be deployed in one or more positions above and below a patient plane during said commissioning.

8. A radiation therapy device as recited in claim 7, said electronic portal imaging device adapted to be deployed below a patient plane a radiation source during said therapy.

9. A radiation therapy system, comprising:
   means for delivering radiation to a body;
   a treatment unit adapted to control commissioning of said delivering means and treatment using said delivering means; and
   an electronic portal imaging device for obtaining radiation dose information during said commissioning and said treatment;
   wherein said electronic portal imaging device is adjustable through a patient plane.

10. A system, comprising:
    means for delivering radiation to a body;
    a treatment unit adapted to control commissioning of said delivering means and treatment using said delivering means; and
    an electronic portal imaging device for obtaining radiation dose information during said commissioning and said treatment;
    said electronic portal imaging device including an imaging panel adapted to be deployed in a patient plane during said commissioning.

11. A system according to claim 10, said electronic portal imaging device including an imaging panel adapted to be deployed in one or more positions above and below a patient plane during said commissioning.

12. A system according to claim 11, said electronic portal imaging device including an imaging panel adapted to be deployed below a patient plane and between a patient and a radiation source during said treatment.

13. A radiation therapy method, comprising:
    providing a linear accelerator for providing radiation to a body; and
    providing an electronic portal imaging device operably coupled to said linear accelerator, said electronic portal imaging device adapted for use in commissioning said radiation therapy device and adapted for use in dosimetry applications during therapy; wherein said electronic portal imaging device is adjustable through a patient plane.

14. A radiation therapy method, comprising:
    providing a linear accelerator for providing radiation to a body; and
    providing an electronic portal imaging device operably coupled to said linear accelerator, said electronic portal imaging device adapted for use in commissioning said radiation therapy device and adapted for use in dosimetry applications during therapy;
    said electronic portal imaging device adapted to be deployed in a patient plane during said commissioning.

15. A radiation therapy method as recited in claim 14, said electronic portal imaging device adapted to be deployed in one or more positions above and below a patient plane during said commissioning.

16. A radiation therapy method as recited in claim 15, said electronic portal imaging device adapted to be deployed below a patient plane and a radiation source during said therapy.

17. A radiation therapy method, comprising:
    providing a linear accelerator for providing radiation to a body; and
    providing an electronic portal imaging device operably coupled to said linear accelerator, said electronic portal imaging device adapted for use in patient exit dosimetry of said radiation therapy device and adapted for use in dosimetry applications during therapy treatment; wherein said electronic portal imaging device is adjustable through a patient plane.

* * * * *